US010300206B2

(12) United States Patent
Bergens et al.

(10) Patent No.: US 10,300,206 B2
(45) Date of Patent: May 28, 2019

(54) DOSE SETTING MECHANISM AND MEDICAMENT DELIVERY DEVICE COMPRISING THE DOSE SETTING MECHANISM

(71) Applicant: CAREBAY EUROPE LTD, Sliema (MT)

(72) Inventors: Thomas Bergens, Ingarö (SE); Anders Wieselblad, Stockholm (SE)

(73) Assignee: SHL MEDICAL AG, Zug (CH)

( * ) Notice: Subject to any disclaimer, the term of this patent is extended or adjusted under 35 U.S.C. 154(b) by 22 days.

(21) Appl. No.: 15/557,974

(22) PCT Filed: Mar. 9, 2016

(86) PCT No.: PCT/EP2016/055003
§ 371 (c)(1),
(2) Date: Sep. 13, 2017

(87) PCT Pub. No.: WO2016/146448
PCT Pub. Date: Sep. 22, 2016

(65) Prior Publication Data
US 2018/0056007 A1 Mar. 1, 2018

(30) Foreign Application Priority Data

Mar. 19, 2015 (SE) ...................... 1550333

(51) Int. Cl.
*A61M 5/24* (2006.01)
*A61M 5/315* (2006.01)
*A61M 5/31* (2006.01)

(52) U.S. Cl.
CPC ...... *A61M 5/31541* (2013.01); *A61M 5/3146* (2013.01); *A61M 5/31551* (2013.01);
(Continued)

(58) Field of Classification Search
CPC ............ A61M 5/31541; A61M 5/3146; A61M 5/31551; A61M 5/31563; A61M 5/31591; A61M 5/24
See application file for complete search history.

(56) References Cited

U.S. PATENT DOCUMENTS 5,092,842 A * 3/1992 Bechtold ................. A61M 5/20
604/135
5,279,586 A * 1/1994 Ballwin .............. A61M 5/3158
222/309

(Continued)

FOREIGN PATENT DOCUMENTS

WO 2006/125328 A1 11/2006
WO 2014/187811 A1 11/2014
WO 2015/032775 A1 3/2015

OTHER PUBLICATIONS

International Search Report and Written Opinion for Int. App. No. PCT/EP2016/055003, dated May 19, 2016.

*Primary Examiner* — Nathan R Price
*Assistant Examiner* — Mark Alan Igel
(74) *Attorney, Agent, or Firm* — McDonnell Boehnen Hulbert & Berghoff LLP

(57) ABSTRACT

A dose setting mechanism for a medicament delivery device is presented having a tubular member, a dose drum, coaxial with the tubular member, and being axially and rotationally movable relative to the tubular member, a stop member, coaxial with the tubular member, and axially movable but rotationally locked relative to the tubular member, and further being axially jointly movable with the dose drum, wherein the stop member has a first stop element and in that the dose drum has a second stop element, and wherein the first stop element and the second stop element are configured to interact with each other to limit rotation of the dose drum to a predetermined angular interval.

19 Claims, 13 Drawing Sheets

(52) U.S. Cl.
CPC .... *A61M 5/31563* (2013.01); *A61M 5/31591* (2013.01); *A61M 5/24* (2013.01); *A61M 5/31561* (2013.01); *A61M 5/31575* (2013.01); *A61M 5/31585* (2013.01); *A61M 2005/2407* (2013.01); *A61M 2205/581* (2013.01); *A61M 2205/582* (2013.01)

(56) References Cited

U.S. PATENT DOCUMENTS

| | | | | |
|---|---|---|---|---|
| 5,921,966 | A * | 7/1999 | Bendek | A61M 5/24 604/207 |
| 6,221,053 | B1 * | 4/2001 | Walters | A61M 5/31551 604/208 |
| 8,545,456 | B2 | 10/2013 | Kirchhofer et al. | |
| 8,608,709 | B2 * | 12/2013 | Moller | A61M 5/24 604/110 |
| 2002/0052578 | A1 * | 5/2002 | Moller | A61M 5/24 604/208 |
| 2012/0283647 | A1 * | 11/2012 | Cronenberg | A61M 5/31595 604/207 |
| 2018/0028757 | A1 * | 2/2018 | Plumptre | A61M 5/31535 |

* cited by examiner

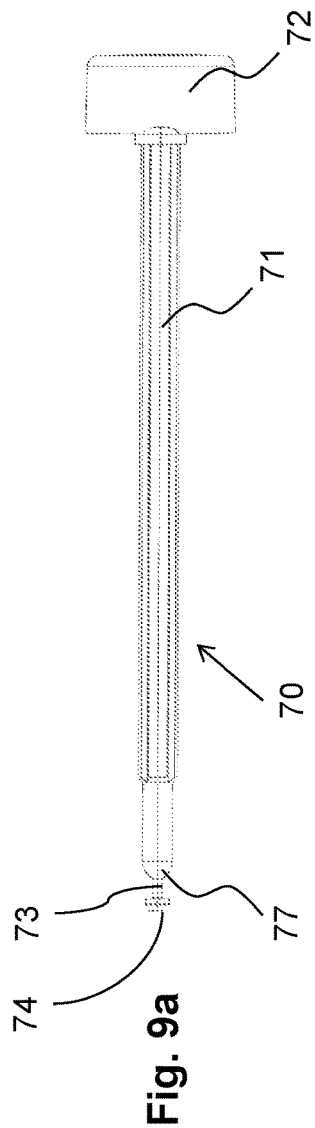
Fig. 9a
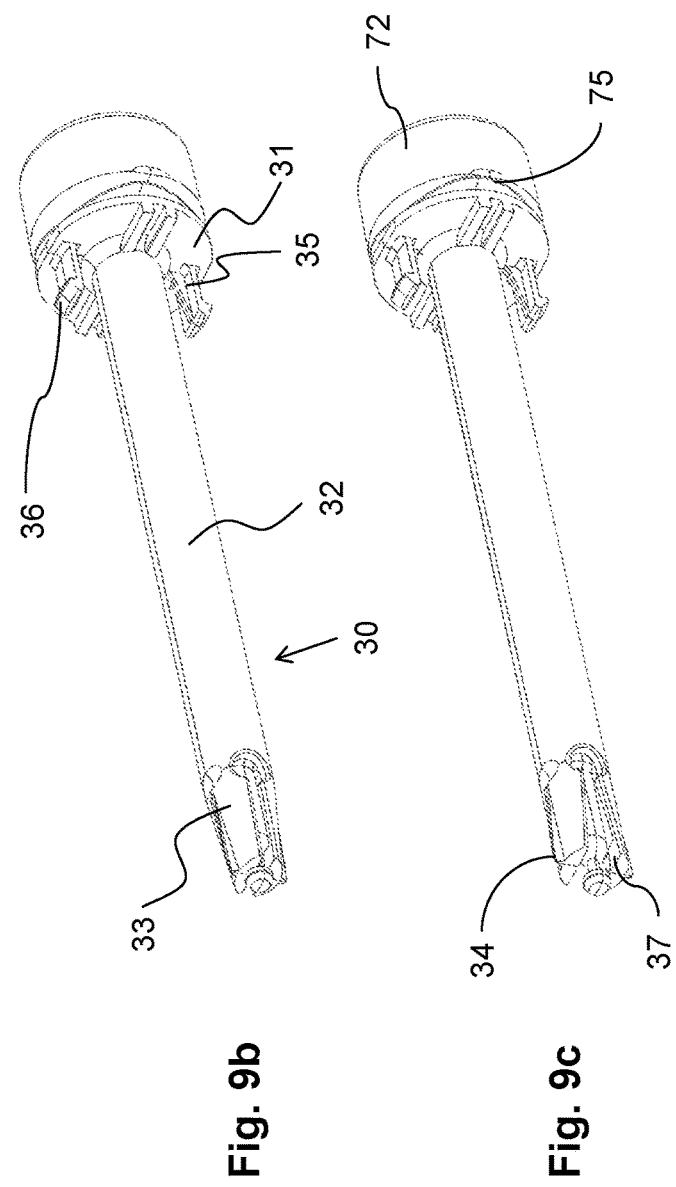
Fig. 9b
Fig. 9c

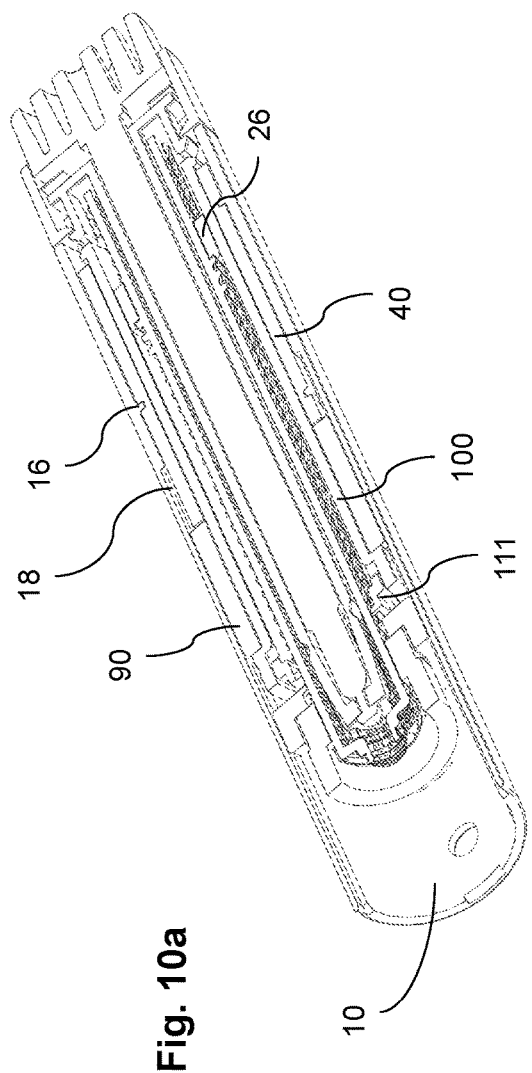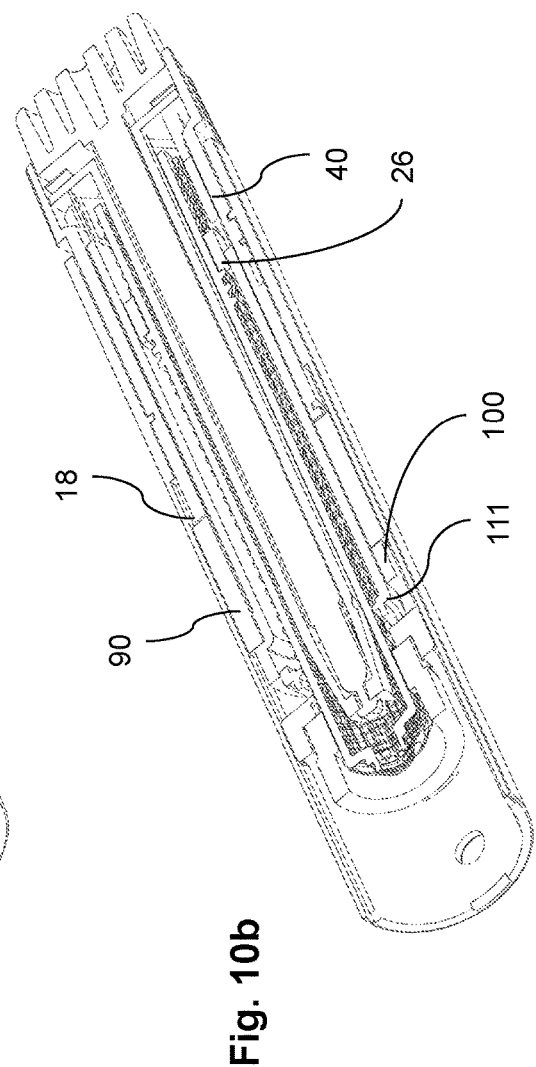

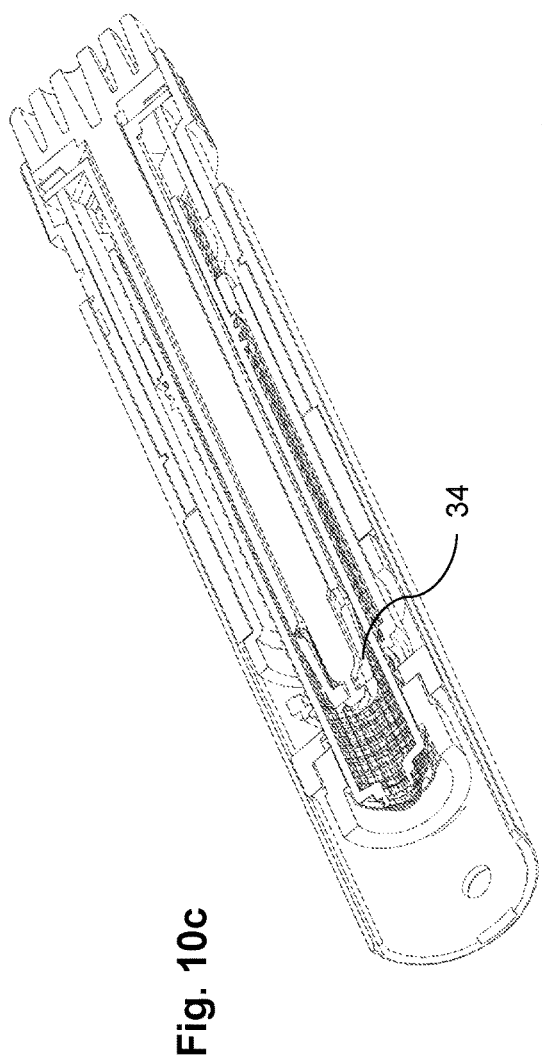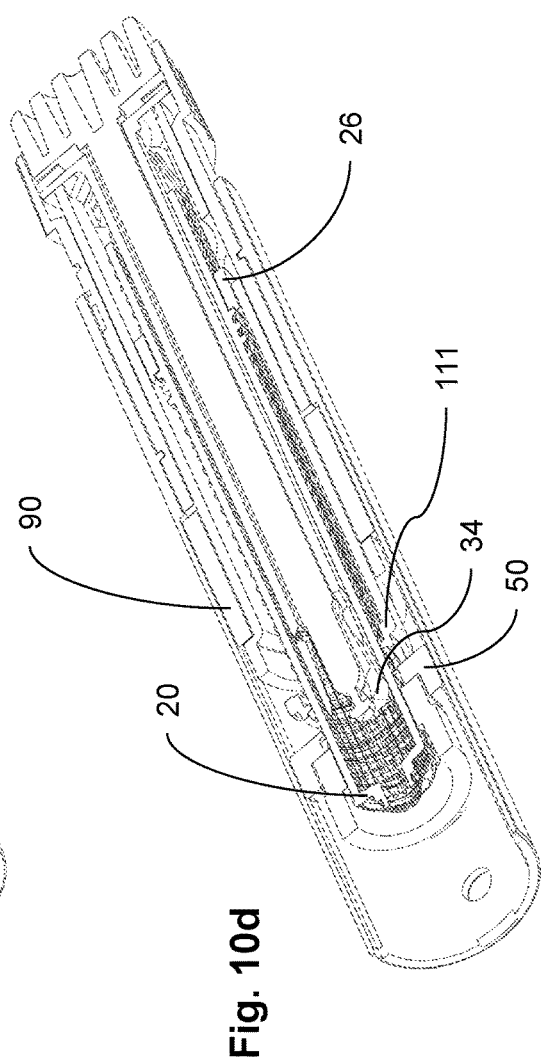
Fig. 10c
Fig. 10d

DOSE SETTING MECHANISM AND MEDICAMENT DELIVERY DEVICE COMPRISING THE DOSE SETTING MECHANISM

CROSS REFERENCE TO RELATED APPLICATIONS

The present application is a U.S. National Phase Application pursuant to 35 U.S.C. § 371 of International Application No. PCT/EP2016/055003 filed Mar. 9, 2016, which claims priority to Swedish Patent Application No. 1550333-7 filed Mar. 19, 2015. The entire disclosure contents of these applications are herewith incorporated by reference into the present application.

TECHNICAL FIELD

The present disclosure relates to a dose setting mechanism for a medicament delivery device and in particular to a dose setting mechanism having a predetermined fixed dose. The disclosure also relates to a medicament delivery device comprising such a dose setting mechanism.

BACKGROUND

There are numerous devices for delivering medicament on the market where the medicament is arranged in a container, such as a syringe, a cartridge or the like, and wherein the medicament is ejected through a delivery member, such as a needle or a nozzle, by driving a movable stopper inside the container.

The stopper is exposed to pressure, i.e. pushed into the compartment by a plunger rod. Actuation of the plunger rod could be done manually, as in the case of standard handheld syringes, or by pressure means such as springs. The latter is common in automatic or semi-automatic injectors. An example of a manual delivery device is the so called pen-injector.

Different dose setting mechanisms have been developed for pen injectors to allow control of the dose to be delivered. Different factors determine the required amount of medicament, such as the severity of the ailment, the required effect, the body mass of the user, etc. One important aspect of dose setting is to prevent the user from over-dosing the drug. A solution to the problem is presented in U.S. Pat. No. 8,545,456, wherein a pen injector is disclosed, having a dosage setting member that is rotated along a thread, relative to a casing. A rotational block is provided, which rotational block comprises a first and a second rotational stopper, such that when the dosage member has been rotated a certain distance, i.e. to an end position, the first and the second rotational stoppers abut against each other to prevent further rotation in that direction. The range of rotation allowed is set during design of the device and determines the maximum dose that may be set.

However, there are alternative solutions for providing a maximum dose stop, as will be described herein.

SUMMARY

An object of the present disclosure is to provide a medicament delivery device wherein the drawbacks of the state of the art devices are remedied.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

An embodiment of the present disclosure relates to a dose setting mechanism for a medicament delivery device, which dose setting mechanism comprises, a tubular member; a dose drum, coaxial with the tubular member, and being axially and rotationally movable relative to the tubular member; a stop member, coaxial with the tubular member, and axially movable but rotationally locked relative to the tubular member, and further being axially jointly movable with the dose drum; wherein said stop member comprises a first stop element and in that said dose drum comprises a second stop element, and wherein said first stop element and said second stop element are configured to interact with each other to limit rotation of the dose drum to a predetermined angular interval.

In an aspect of the embodiment the dose drum is in a first threaded connection with the tubular member.

In an aspect of the embodiment the stop member is generally tubular and comprises a track follower in engagement with a longitudinal track of the tubular member such that rotational movement of the dose drum causes a rotationally locked, axial movement, of the stop member relative to the tubular member.

In an aspect of the embodiment the first stop element projects distally from a distally-facing annular end of the stop member and wherein the second stop element projects proximally from a proximally-facing annular end of the dose member.

In an aspect of the embodiment the predetermined angular interval is defined by an angle between an initial angular position and a full dose angular position of said second stop element relative to the first stop element.

In an aspect of the embodiment the second stop element abuts the first stop element in said full dose angular position.

In an aspect of the embodiment a distally-facing part of the stop member and a proximally-facing part of the dose drum are arranged with shaped surfaces such that rotation of the dose drum relative to the stop member causes a tactile and/or audible feedback signal as the shaped surfaces slide against each other.

In an aspect of the embodiment one of said shaped surfaces comprises a mating segment in a predetermined angular position and wherein the other of said shaped surfaces comprises a corresponding mating segment such that rotation of the dose drum relative to the stop member causes a tactile and/or audible feedback signal as the corresponding mating surface interacts with the mating segment in the predetermined angular position.

In an aspect of the embodiment the predetermined position of the mating segment corresponds to an intermediate priming position between the initial angular position and the full dose angular position.

In an aspect of the embodiment the dose setting mechanism further comprises a dose drum follower and a dose blocker sleeve, wherein the dose drum follower is axially and rotationally connected to the dose drum, and wherein the dose blocker sleeve is axially movable, but rotationally locked relative to the dose drum follower.

In an aspect of the embodiment the dose drum follower comprises distal, radially resilient holding elements configured to interact with a slanting ledge of the dose drum, the dose drum follower further comprising a proximal support ring such that the stop member is distally biased against the dose drum by the support ring of the dose drum follower through the interaction between the radially flexible holding elements and the slanting ledge.

In an aspect of the embodiment the stop member is positioned radially outside an elongated half-tubular sleeve of the dose drum follower, and wherein the half-tubular sleeve connects the proximal support ring with a distal forked sleeve of the dose drum follower.

In an aspect of the embodiment the forked sleeve comprises distally extending arms, which distally extending arms comprise the holding elements, and wherein the distally extending arms are resilient in the radial direction.

In an aspect of the embodiment the holding elements are arranged with slanting proximal and distal surfaces.

In an aspect of the embodiment the dose setting mechanism comprises a threaded plunger rod and a blocking ring, wherein said dose blocker sleeve is in a second threaded connection with the threaded plunger rod, and wherein the blocking ring is fixedly connected to the threaded plunger rod.

A further embodiment of the present disclosure relates to a medicament delivery device comprising a dose setting mechanism according to any of the above-mentioned embodiments or aspects.

Other aspects, features, and advantages will be apparent from the summary above, as well as from the description that follows, including the figures and the claims.

BRIEF DESCRIPTION OF THE DRAWINGS

The figures below disclose an embodiment of the disclosure for illustrational purposes only. In particular, the disclosure within the figures is not meant to limit the range of protection of the disclosure. The embodiment shown may be modified in different ways within the scope of the claims.

FIG. 9a-c show perspective views of an actuation mechanism of the medicament delivery device according to FIG. 1;

FIG. 10a-e show cross-sectional views of the medicament delivery device at different stages of dose setting and dose delivery;

DETAILED DESCRIPTION

Figure 1:
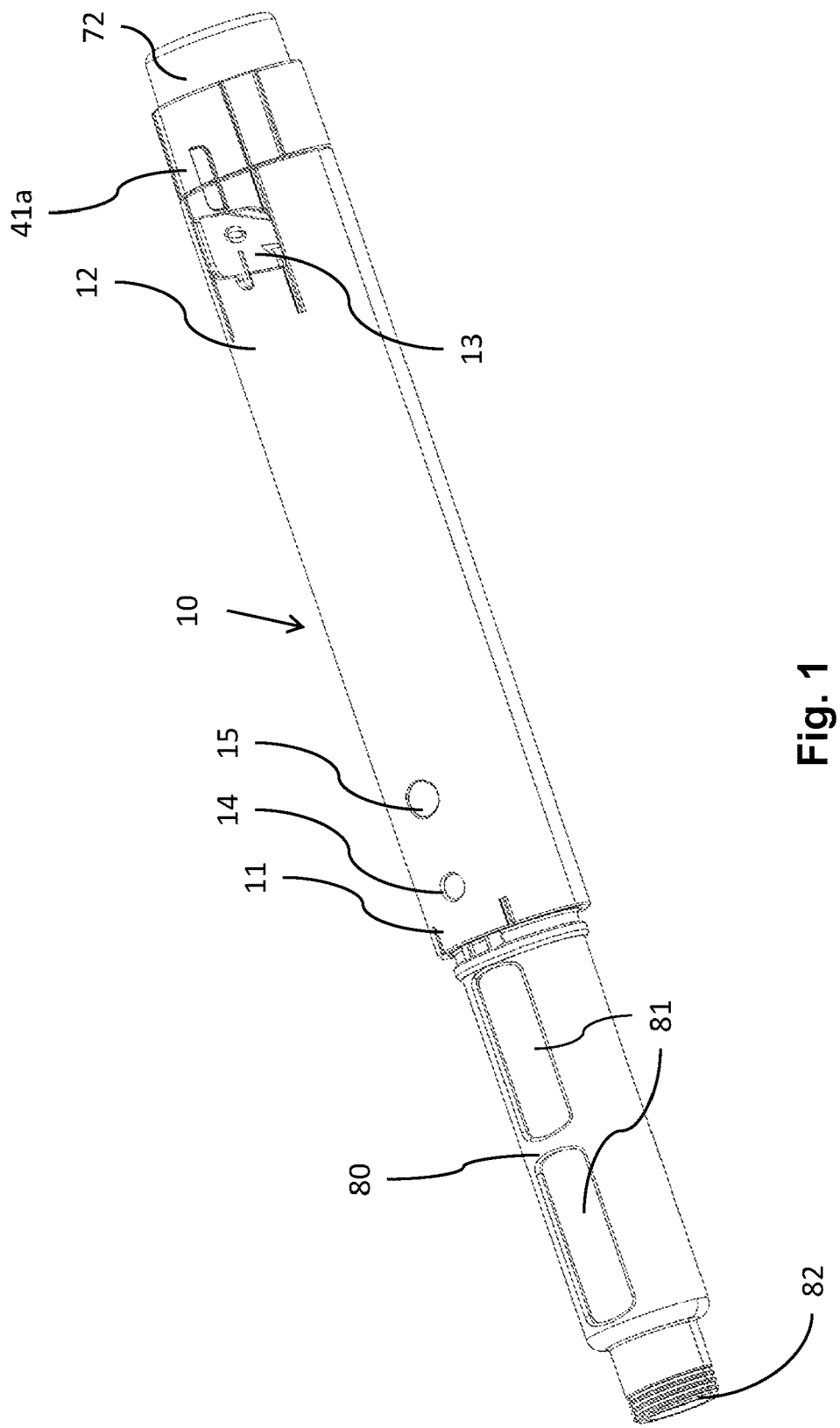
FIG. 1 shows a perspective view of a medicament delivery device according to a preferred embodiment of the disclosure, shown in an initial state.

FIG. 1 shows a perspective view of a medicament delivery device according to an embodiment of the disclosure. The medicament delivery device has a proximal end and a distal end and comprises a housing 10 having a proximal part or end 11 and a distal part or end 12. In the assembled state of the medicament delivery device, the housing 10 forms part of the outer surface or appearance of the medicament delivery device, but since the herein-described technical features of the housing may be comprised in any sleeve-like or tubular member, the housing 10 will hereinafter be referred to as the tubular member 10.

The medicament delivery device further comprises a medicament container holder 80 which accommodates a medicament container. The medicament container holder 80 also forms part of the outer surface or appearance of the medicament delivery device. The proximal part of the container holder 80 is further arranged with a neck 82 at its proximal end, for attaching a per se known and conventional delivery member, e.g. an injection needle (not shown). It is to be understood that other types of connection members, such as bayonet fittings, luer-lock fittings, and the like may be arranged. Also, the medicament container may have an injection needle integrated in its body, in which case the coupling for the delivery member may be omitted.

A removable cap (not shown) may be provided to cover the proximal end of the device, and the proximal end of the medicament container holder 80, when the medicament delivery device is not in use.

Through window 81, a user can see a medicament container accommodated in the medicament container holder 80, allowing the user to view the remaining amount of a drug in the medicament container. A distal part of the medicament container may reach into the proximal part of the tubular member 10 when the medicament container holder is connected to the tubular member 10.

Furthermore, at the distal end 12 of the tubular member 10, a dose window 13 is provided that shows a set dose to the user, as described in more detail below. At the distal end 12 of the tubular member 10, a movable dose setting knob 41a is also arranged.

FIG. 1 shows the medicament delivery device in an initial state. When the user grasps the dose setting knob 41a and rotates it in a first direction to set a dose, the dose setting knob 41a and other components move distally, as will be explained in detail below.

Figure 2:
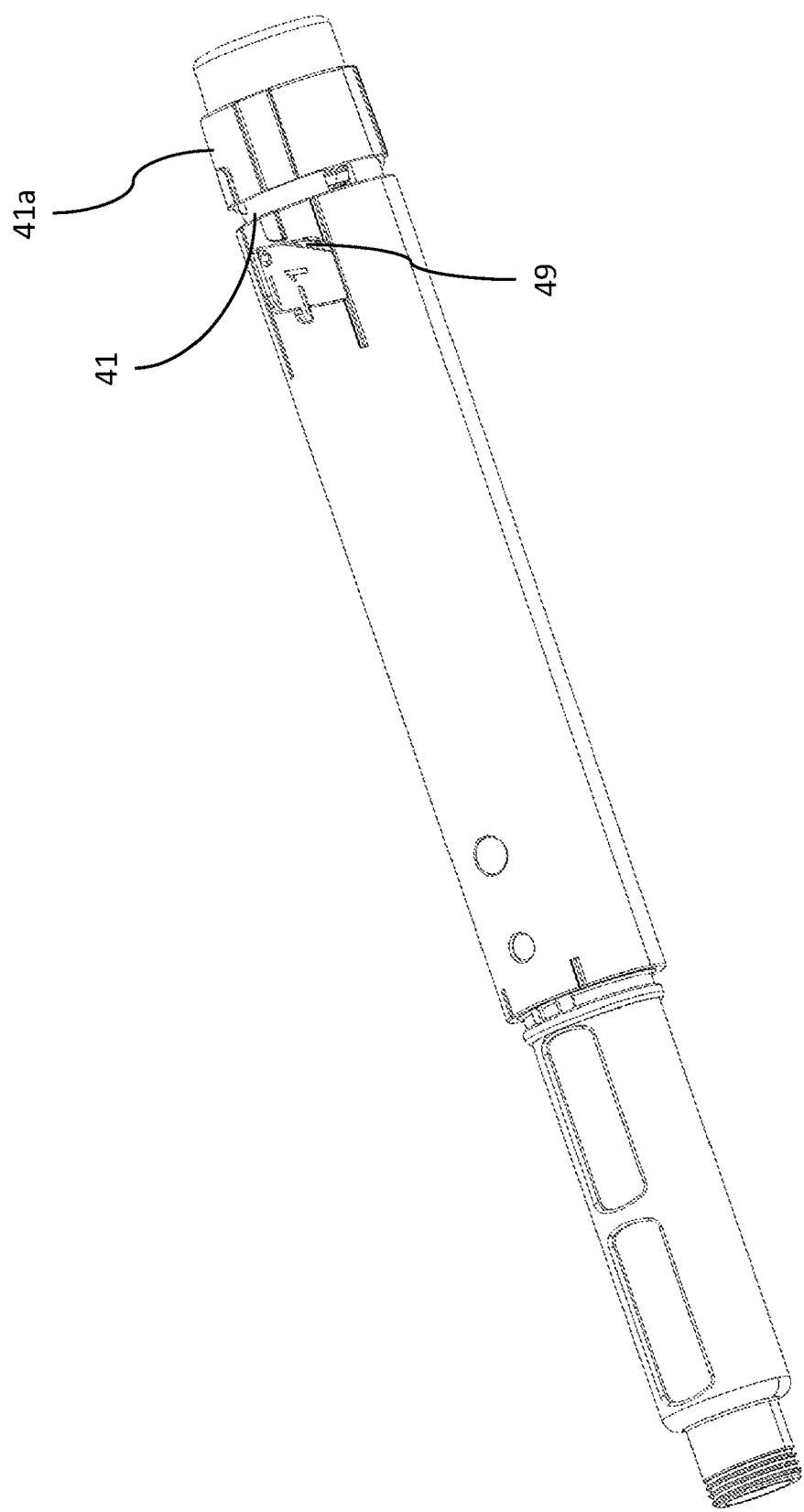
FIG. 2 shows a perspective view of a medicament delivery device according to the preferred embodiment of FIG. 1, shown in a state where a priming dose has been set.

FIG. 2 shows a perspective view of the medicament delivery device in a priming dose state, i.e. when a priming dose has been set. A priming dose is a small dose intended to evacuate any air from the container before the device is used. When priming the device, the delivery member should be pointed upwards so that any air trapped inside may easily escape through the delivery member.

Figure 3:
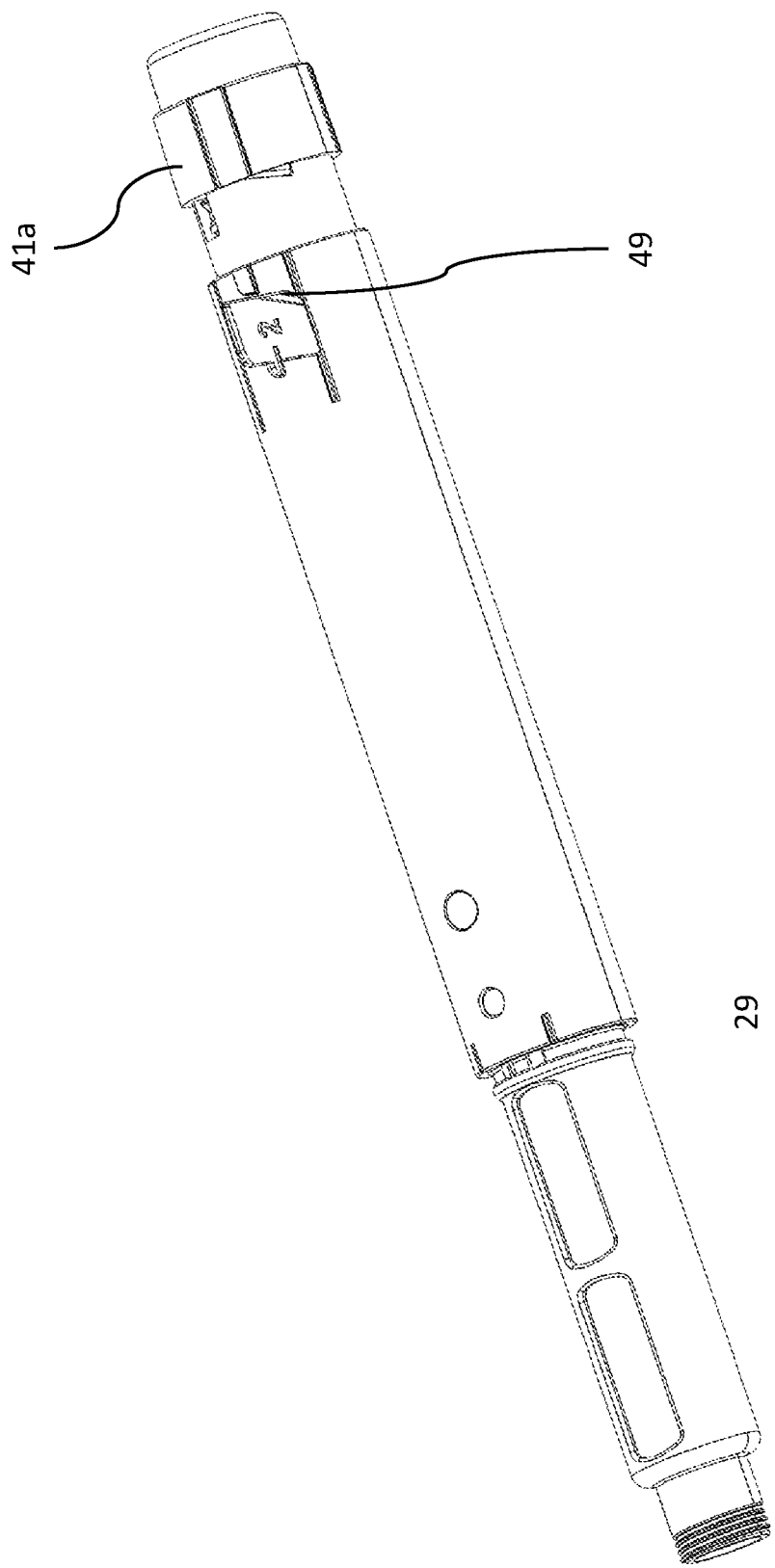
FIG. 3 shows a perspective view of a medicament delivery device according to the preferred embodiment of FIG. 1, shown in a full dose state

FIG. 3 shows a perspective view of the medicament delivery device in a full dose state, i.e. when the device has been primed and the user intends to administer the prescribed dose that the device was designed to deliver.

Figure 4:
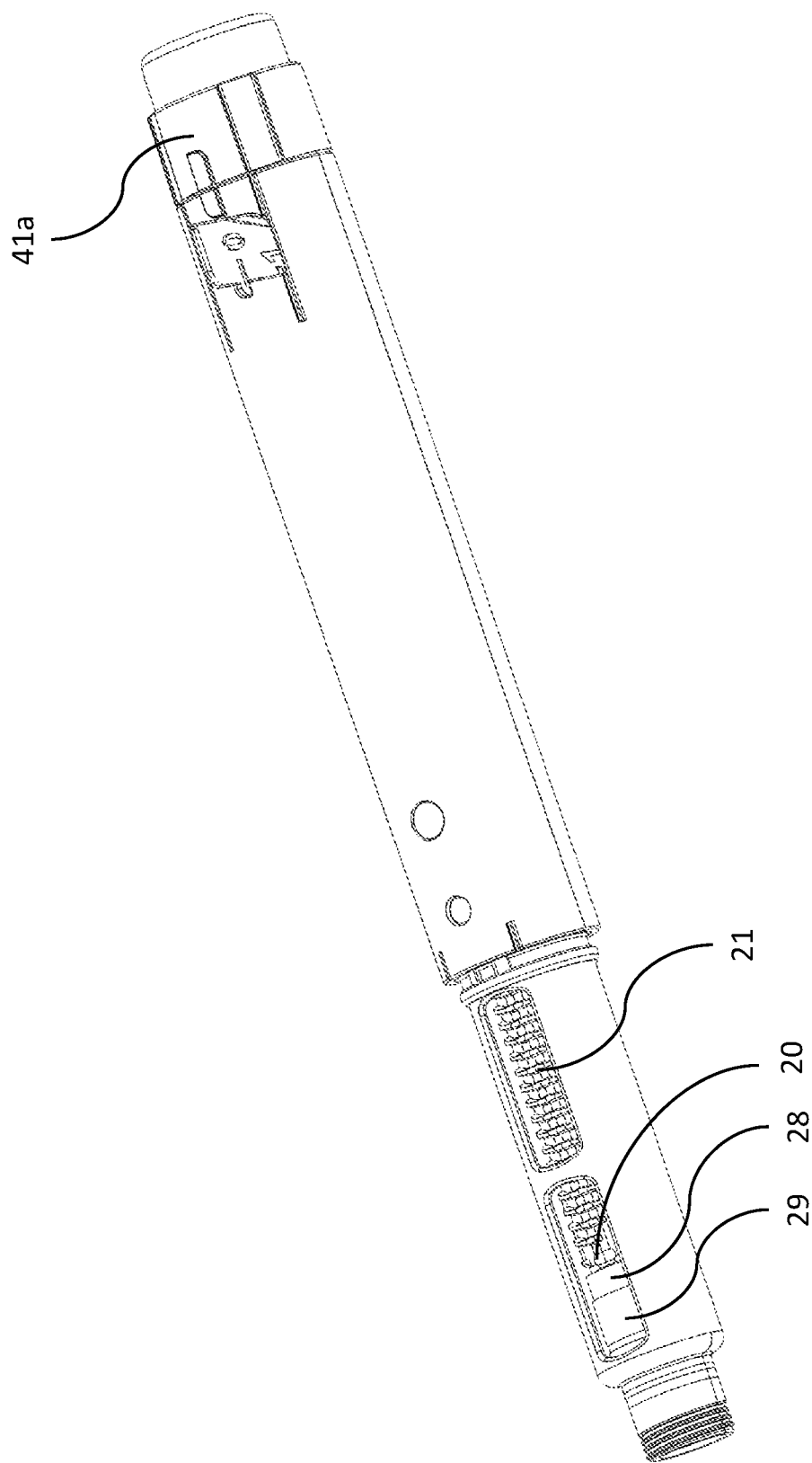
FIG. 4 shows a perspective view of a medicament delivery device according to the preferred embodiment of FIG. 1, shown after all doses have been delivered and the medicament container is empty.

FIG. 4 shows a perspective view of the medicament delivery device in a final state, having expelled a number of doses and having emptied the medicament container. As can be seen, the dose setting knob 41a and the components linked therewith have been moved proximally and the dose setting knob 41a is again in its initial position. However, a threaded plunger rod 20 of the medicament delivery device has also been displaced in the proximal direction, pushing a stopper 29 into view within the medicament container. The stopper 29 can be seen located at the proximal end of the medicament container, and part of the plunger rod 20, having an outer thread 21, can be seen through windows 81.

The medicament container holder 80 is arranged with distal attachment means for connecting or attaching it to the proximal part 11 of the tubular member 10. In the embodiment shown the attachment means comprises a protrusion 83 (see FIG. 5) fitting into a corresponding recess 14. Alternatively, the connection could be designed as a protrusion on the inside of the tubular member 10 that connects with a corresponding recess on the medicament container holder 80. It is also to be understood that other attachment members may be utilized, such as bayonet fittings, threads, or the like for attaching the medicament container holder 80 to the tubular member 10.

Figure 5:
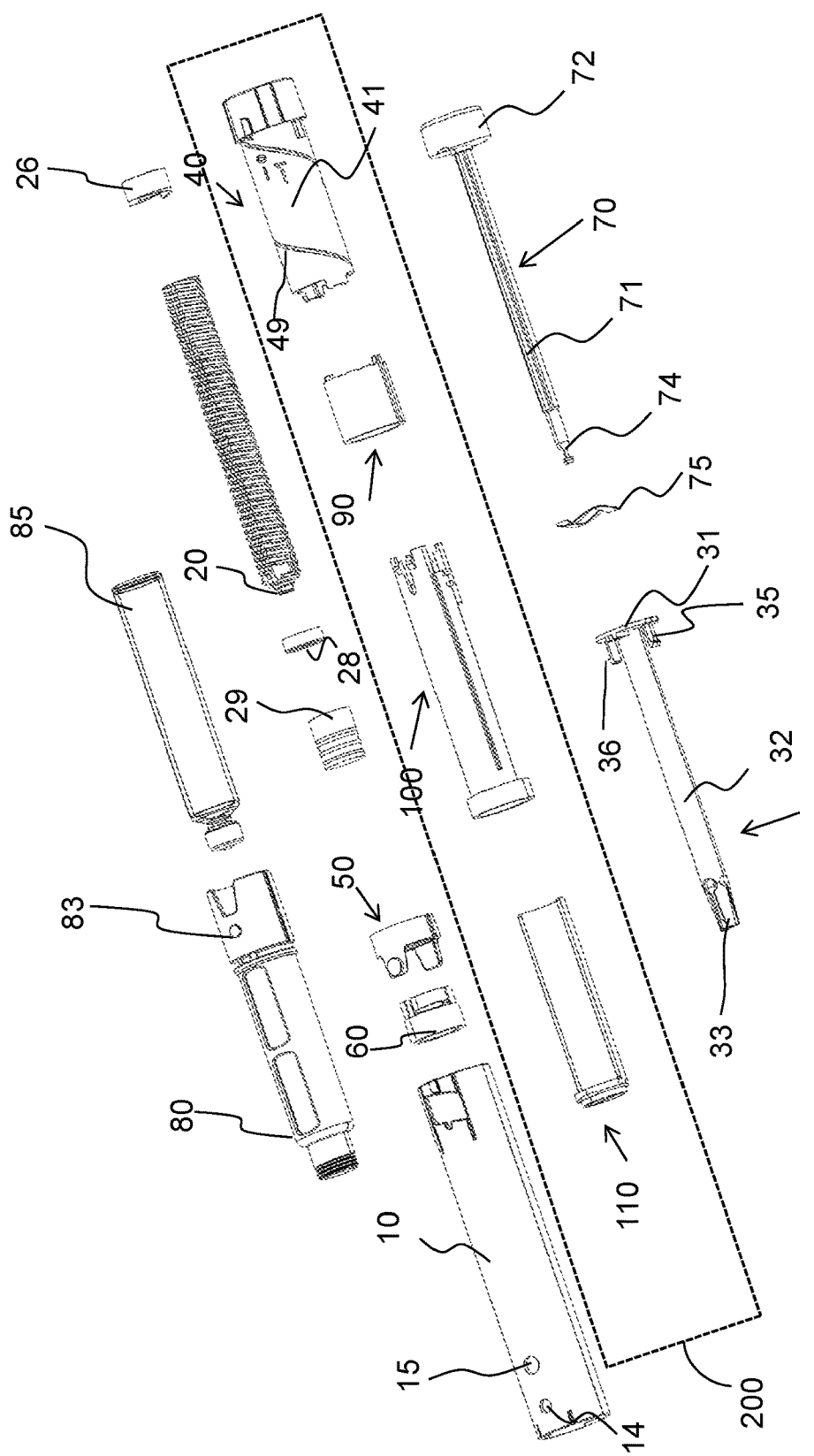
FIG. 5 shows an exploded perspective view of the components of the medicament delivery device of previous figures.

FIG. 5 serves as an overview of the constituent parts of the complete medicament delivery device, except for a medicament delivery member, which is not shown.

Figure 6:
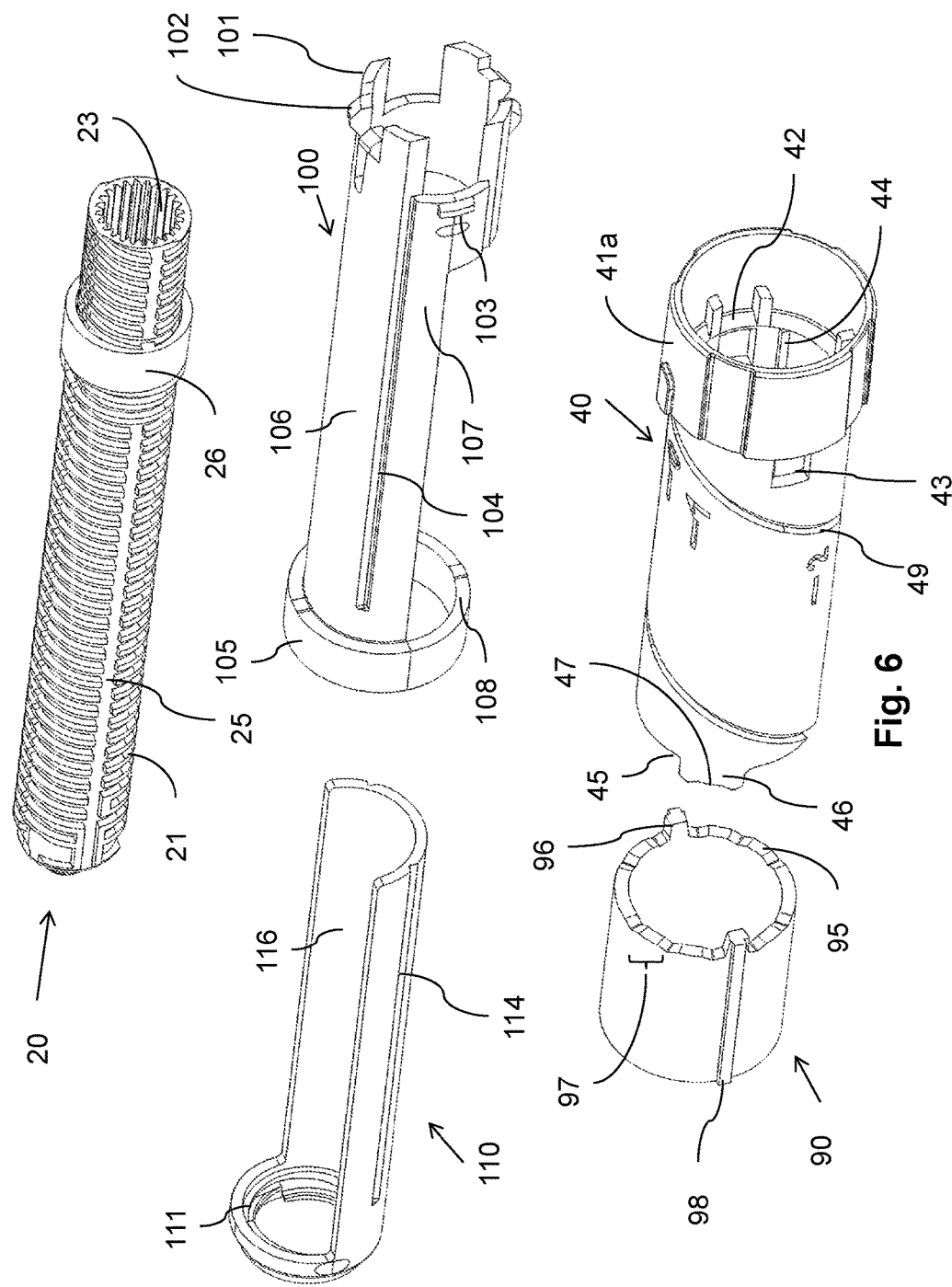
FIG. 6 shows an exploded view of a part of the medicament delivery device according to FIG. 1.

FIGS. 5 and 6 show the elongated plunger rod 20, which is arranged inside the tubular member 10 and has a longitudinal axis generally corresponding to the longitudinal axis of the medicament delivery device. The plunger rod 20 is arranged with the outer thread 21 on at least part of its outer surface. The plunger rod 20 is further arranged with at least one longitudinal groove 25. In the present embodiment, two such grooves 25 are provided on opposite sides of the plunger rod. The proximal end of the plunger rod 20 is arranged with a spinner 28, (FIG. 5) configured as an interface between the stopper 29 and the plunger rod 20 for reducing frictional resistance arising when the plunger rod 20 rotates in relation to the stopper 29. The stopper 29 is movably received inside the medicament container 85. A blocking ring 26, having longitudinal splines on its inner circumferential surface, is mounted on a distal part of the plunger rod 20 at a predetermined distance from a dose blocker sleeve 110, wherein the longitudinal splines engage the longitudinal grooves 25 of the plunger rod 20. The blocking ring 26 is thus rotationally locked to the plunger rod 20.

FIG. 6 further shows a tubular dose drum 40, an annular, or tubular, stop member 90, a dose drum follower 100, and a dose blocker sleeve 110, which together form a dose setting assembly 200 (FIG. 5). The dose drum 40 is in a first threaded connection with the tubular member 10, whereby a proximal part of the dose drum 40 is arranged with a spirally extending groove 49 adapted to interact with a protrusion, or spirally extending ledge 16 (FIG. 10a), on the inside surface of the tubular member 10, such that rotation of the dose drum 40 relative to the tubular member 10 also causes the dose drum to move axially, relative to the tubular member.

The dose drum 40 is further provided with indicia on the outer circumferential surface. As the dose drum 40 moves relative to the tubular member 10, the indicia are shown through the dose window 13, informing the user about the set dose. In the embodiment shown in the drawings, the indicia are: 0—initial state, 1—priming dose state, and 2—full dose state. When the dose drum is assembled with the tubular member 10, the dose knob 41a, at the distal part of the dose drum, is accessible to the user, allowing him/her to rotate the dose drum to set a dose. The outer circumferential surface of the dose knob 41a is preferably flush with the outer surface of the tubular member 10.

A circumferential slanting ledge 42 is arranged on the inside surface of the distal part of the dose drum 40. The slanting ledge 42 is configured to interact with radially flexible holding elements 102 on distally extending arms 101 of the dose drum follower 100, as will be explained below in detail.

Cut-outs are arranged in the circumferential surface, adjacent the dose knob 41a. The cut-outs 43 are configured to accommodate radially protruding ledges 103 of the dose drum follower 100. A certain axial play between the cut-outs of the dose drum 40 and the ledges of the dose drum follower 100 creates a gap between a proximally facing surface of the ledges 103 and a distally facing edge of the cut-outs 43. This axial play allows the dose drum follower 100 to be slightly proximally displaced with respect to the dose drum 40 during medicament delivery, which will be further explained below. The proximally facing edges of the cut-outs interact with the ledges to prevent the dose drum follower from exiting the dose drum in the distal direction. Longitudinally extending ribs 44 on the inner surface of the dose drum 40 interact with longitudinally extending grooves 104, 114 on the outer surface of the dose drum follower 100 and of the dose blocker sleeve 110 such that the dose drum follower and the dose blocker sleeve are longitudinally movable, but rotationally fixed, relative to the dose drum.

The dose drum follower 100 is arranged coaxially with, and radially inside, the dose drum 40. The dose drum follower 100 comprises a proximal support ring 105 and a distal forked sleeve 107, which support ring and forked sleeve are connected by a longitudinally elongated half-tubular sleeve 106. The outer surface of the elongated half-tubular sleeve is arranged with the longitudinally extending grooves 104. The inner radius of the support ring 105 is generally equal to the outer radius of the half-tubular sleeve, and the outer radius of the support ring 105 is generally equal to the outer radius of the proximal part of the dose drum 40, such that an annular, distally-facing support shelf 108 is formed by the support ring 105. The forked sleeve 107 comprises distally extending resilient arms 101 arranged with holding elements 102, which holding elements protrude radially outwards from the forked sleeve. The holding elements 102 are arranged with slanting proximal and distal surfaces and are configured to interact with the slanting ledge 42 of the dose drum 40. The arms 101 are resilient in the generally radial direction, and consequently the holding elements 102 are also radially resilient. Further to the description above, the ledges 103 are arranged on the outer circumferential surface of the forked sleeve 107 and protrude radially outwards, into the windows 43 of the dose drum 40.

The stop member 90 is preferably annular, or sleeve- or ring-shaped, and arranged coaxially with, and radially outside, the half-tubular sleeve 106 of the dose drum follower 100. The stop member 90 is held between the dose drum follower 100 and the dose drum 40 such that it is supported by its proximal annular surface by the support shelf 108 of the support ring 105, and in abutment by its distal surface, i.e. a distally-facing part 95 of the stop member 90, with a proximally-facing part 45 of the dose drum 40. The dose drum 40 and to the dose drum follower 100 are rotationally movable relative to the stop member 90.

The longitudinal distance between the support shelf 108 and the holding elements 102 is chosen such that the stop member 90 is pressed between the support shelf 108 of the dose drum follower 100, and the proximally-facing part 45 of the dose drum 40. The slanting proximal surfaces of the resilient holding members 102 presses radially outwards against the slanting ledge 42 of the cut-outs 43, resulting in a component force in the longitudinal direction, such that the dose drum follower 100 and the dose drum 40 are resiliently biased towards each other. The stop member is axially jointly movable with the dose drum 40, meaning that an axial displacement of the dose drum 40, causes an axial displacement of the dose drum follower 100 and of the stop member 90.

The distally-facing part 95 of the stop member 90 and the annular proximally-facing part 45 of the dose drum 40 are arranged with shaped surfaces, e.g. in the form of undulations, teeth, notches, etc, such that rotation of the dose drum 40 relative to the stop member 90 causes a tactile and/or audible feedback signal as the shaped surfaces move against each other under the bias of the stop member 90 towards the dose drum 40.

A first stop element 96 projects distally from a distally-facing annular end of the stop member 90 and a second stop element 46 projects proximally from a proximally-facing annular end of the dose member 40.

In the embodiment shown in the drawings, the proximal end of the second stop member 46 and the distally-facing part 95 of the stop member are arranged with the shaped surfaces such that they slide against each other during relative rotation, as described above. Obviously, the device could as well have been designed oppositely, such that the shaped surfaces had been arranged on the distal end of the first stop element 96 and on the proximally-facing part 45 of the dose drum 40, if it had been preferred to have the first stop element 96 slide against the dose drum 40 instead.

Figure 7A:
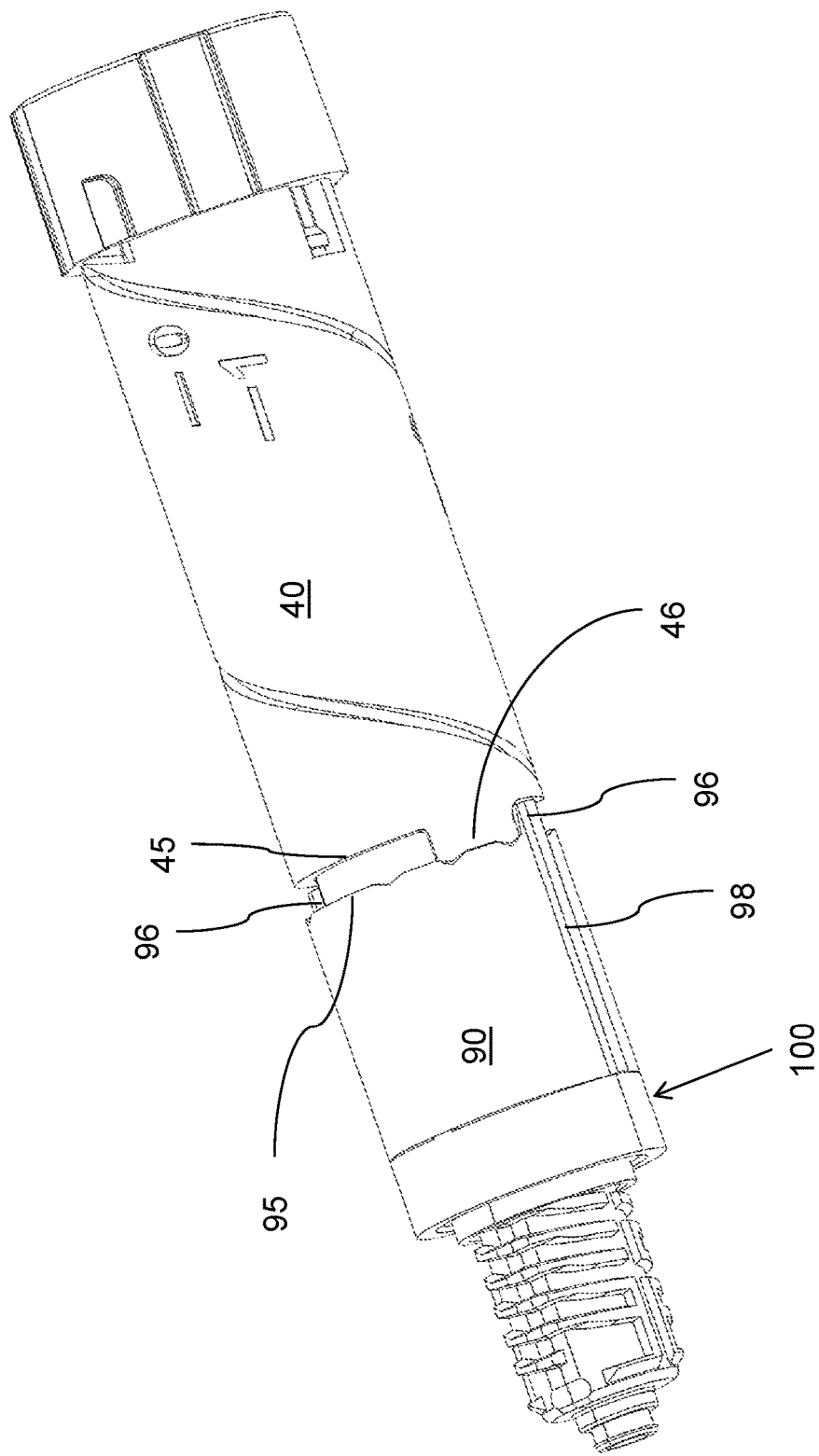
FIG. 7a shows a perspective view of the dose setting mechanism in an initial state of the medicament delivery device of FIG. 1.
Figure 7B:
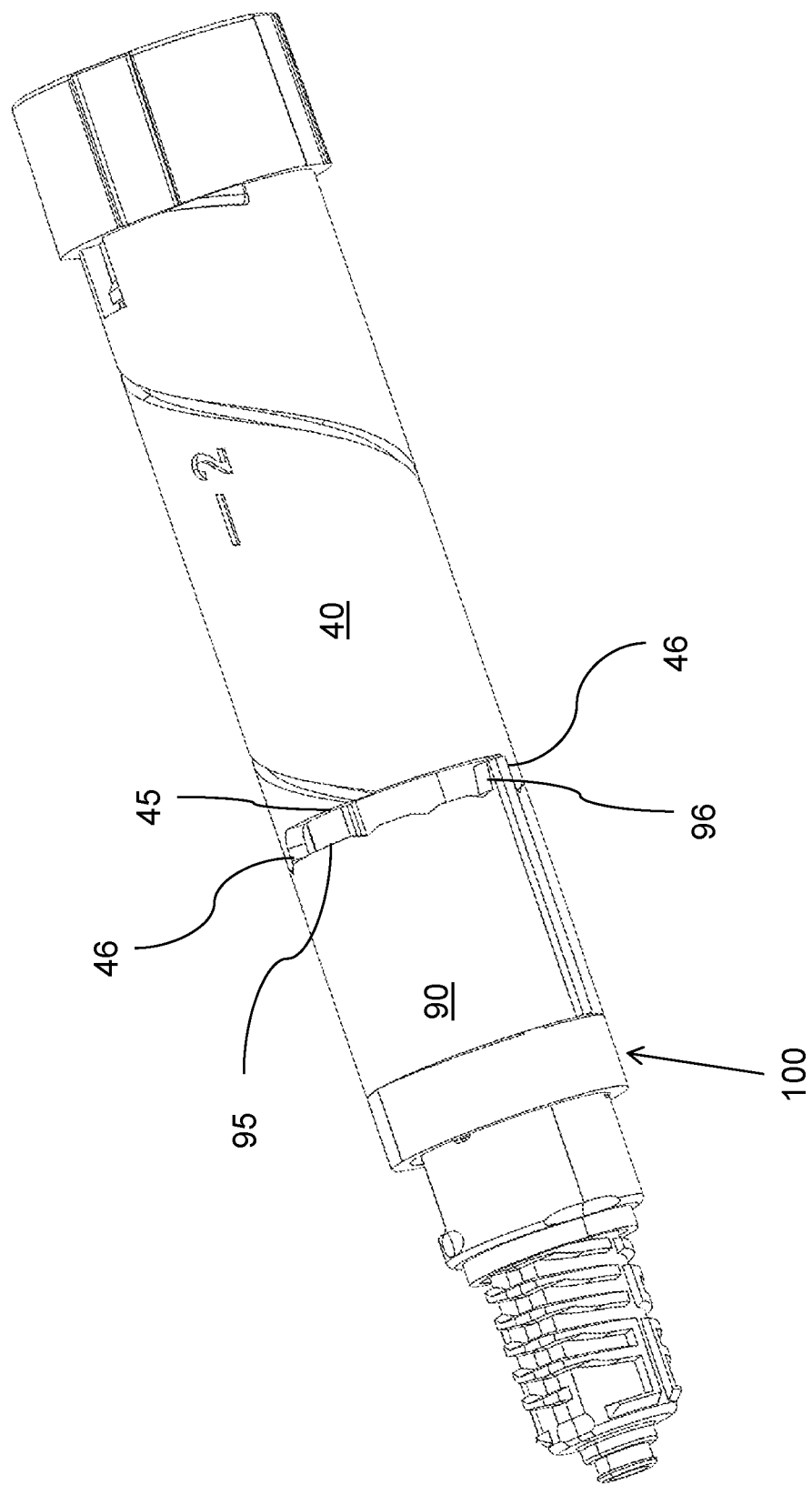
FIG. 7b shows a perspective view of the dose setting mechanism of the medicament delivery device of FIG. 3.

FIGS. 7a and 7b show a perspective view of the dose drum 40, the dose drum follower 100 and the stop member 90. The stop member is arranged with a track follower 98, e.g. a radial protrusion, configured to engage a longitudinal track 18 of the tubular member 10 (FIG. 10a, b), such that the stop member is rotationally fixed relative to the tubular member 10. FIG. 7a shows an initial state of the medicament delivery device, defined as the relative positions of the various components, except for the plunger rod 20 and the blocking ring 26, before a dose is set. Rotation of the dose drum 40 causes it to climb the protrusion 16, via the first threaded connection, bringing the dose drum follower 100 along axially. Since the stop member 90 is axially jointly movable with the dose drum, the stop member is also displaced axially in relation to the tubular member 10. However, the stop member 90 moves rotationally locked relative to the tubular member. The maximum distance that the stop member 90 may be displaced axially is predetermined and set during manufacturing and assembly of the medicament delivery device. The distance depends on the pitch of the first threaded connection and on a predetermined angular interval. The predetermined angular interval is defined by an angle between an initial angular position and a full dose angular position of the second stop element 46 relative to the first stop element 96.

In the shown embodiment there are two first stop elements 96 and two second stop elements 46, arranged on opposite sides of the stop member 90 and of the dose drum 40, respectively. Since the first stop elements 96 are arranged to block rotation of the dose drum when the second stop elements 46 abut the first stop elements 96, the dose drum may only rotate between the initial angular position to the full dose angular position, and back, which in a preferred embodiment corresponds to a maximum rotation of approximately 120 degrees. FIG. 7b shows the dose setting mechanism in the full dose position, wherein the dose drum has been rotated until the second stop element 96 abuts the first stop element 46.

The device is designed as a fixed dose device, which means that the user is supposed to turn the dose knob 41a until rotation comes to a halt and thereby always receive the same, fixed, dose of medicament. However, if a priming dose is necessary, one of the shaped surfaces may comprise a mating segment 97 in a predetermined angular position and the other of the shaped surfaces may comprise a corresponding mating segment 47, see FIG. 6, such that rotation of the dose drum 40 relative to the stop member 90 causes a tactile and/or audible feedback signal as the corresponding mating surface slides against, and interacts, or mates, with the mating segment in the predetermined angular position. The predetermined angular position may be a priming angular position of the second stop element relative to the first stop element. When the corresponding mating segment reaches the priming angular position of the mating segment, the feedback signal tells the user that he/she has set the priming dose.

As shown in FIG. 6, such mating segments may also be arranged to generate feedback signals at the initial angular position and at the full dose angular position.

The dose blocker sleeve 110 is arranged coaxially with the dose drum follower 100 and comprises a longitudinally elongated half-tubular body 116 having threaded ring 111 at a proximal part thereof. The threaded ring 111 is in a second threaded connection with the outer thread 21 of the plunger rod 20. The half-tubular body 116 of the dose blocker sleeve 110 has a complementary shape to the half-tubular sleeve 106 of the dose drum follower 100, and also has a radius generally equal to the radius of the half-tubular sleeve 106. Therefore, the dose blocker sleeve 110 is rotationally locked, but axially movable in relation to the dose drum follower 100 and to the dose drum 40 because the longitudinal edges of the half-tubular body 116 abut the longitudinal edges of the half-tubular sleeve 106. Consequently, rotation of the dose drum 40 causes rotation of the dose drum follower 100 and of the dose blocker sleeve 110. However, because the pitch of the first threaded connection is greater than a pitch of the second threaded connection, the dose drum 40 and the dose drum follower 100 are displaced faster in the axial direction than the dose blocker sleeve 110, causing a telescopic movement of the telescopic dose setting assembly 200.

In an initial state there is a slight play between a distal annular surface of the threaded ring 111 and a proximal half-annular surface of the half-tubular sleeve 106. In a dose-set state the distal annular surface of the threaded ring 111 is separated from the proximal half-annular surface of the half-tubular sleeve 106 by a distance that corresponds to the set dose and to the difference in pitch between the first and the second threaded connections. Delivery of a set dose of medicament returns the dose blocker sleeve 110 and the dose drum follower 100 to their relative positions of the initial state, but the axial position of the telescopic dose setting assembly 200 relative to/along the plunger rod 20 will change with each successive delivered dose, as will be explained in detail below.

The distal annular surface of the threaded ring 111 is further provided with a sawtooth structure configured to engage a corresponding sawtooth structure of a proximal surface of the blocking ring 26. In an unused medicament delivery device, the threaded ring 111 is arranged at a predetermined distance from the blocking ring 26, which distance corresponds to the total amount of medicament in the medicament container. Each time a dose is set the dose blocker sleeve 110 climbs the threads 21 of the plunger rod 20, reducing the distance between the threaded ring 111 and the blocking ring 26. When the dose is expelled, the dose blocker sleeve 110 retains its axial position along the plunger rod 20, as will be explained below. Thus if a user attempts to set a dose that exceeds the remaining amount of medicament in the medicament container, the sawtooth structure of the threaded ring 111 will engage the sawtooth structure of the blocking ring 26 and provide a rotational stop to the dose setting mechanism. Since the blocking ring 26 is rotationally locked to the plunger rod 20, further rotation of the dose blocker sleeve 110 is blocked, and consequently further dose setting via the dose setting assembly 200 is also blocked. Smooth surfaces instead of a sawtooth interface would have caused the dose blocker sleeve 110 and the blocking ring 26 to become attached to each other by screw-tightening.

The plunger rod 20 fits into a coaxial insert 50, arranged with a central passage 51, (FIG. 8) the center of which coincides with the longitudinal axis of the medicament delivery device. The central passage 51 of the thread insert is arranged with an inner thread 52 corresponding to the outer thread 21 of the plunger rod 20. The outer surface of the insert 50 comprises at least one protrusion 53, fitting into corresponding recesses 15 (FIG. 5) on the inner surface of the tubular member 10. The protrusion 53 locks the insert 50 to the tubular member 10. As shown in FIG. 5, the recess 15 in the tubular member may be formed as a through-hole.

The insert 50 further comprises a central bore 54 on the proximal side of the thread insert 50. The diameter of the central bore 54 is larger than the diameter of the central passage 51 so that a stepped configuration between the central passage and the central bore is provided. The inner circumferential surface of the central bore 54 is arranged with a circumferentially extending ratchet 55 having sawtooth-shaped teeth.

Figure 8:
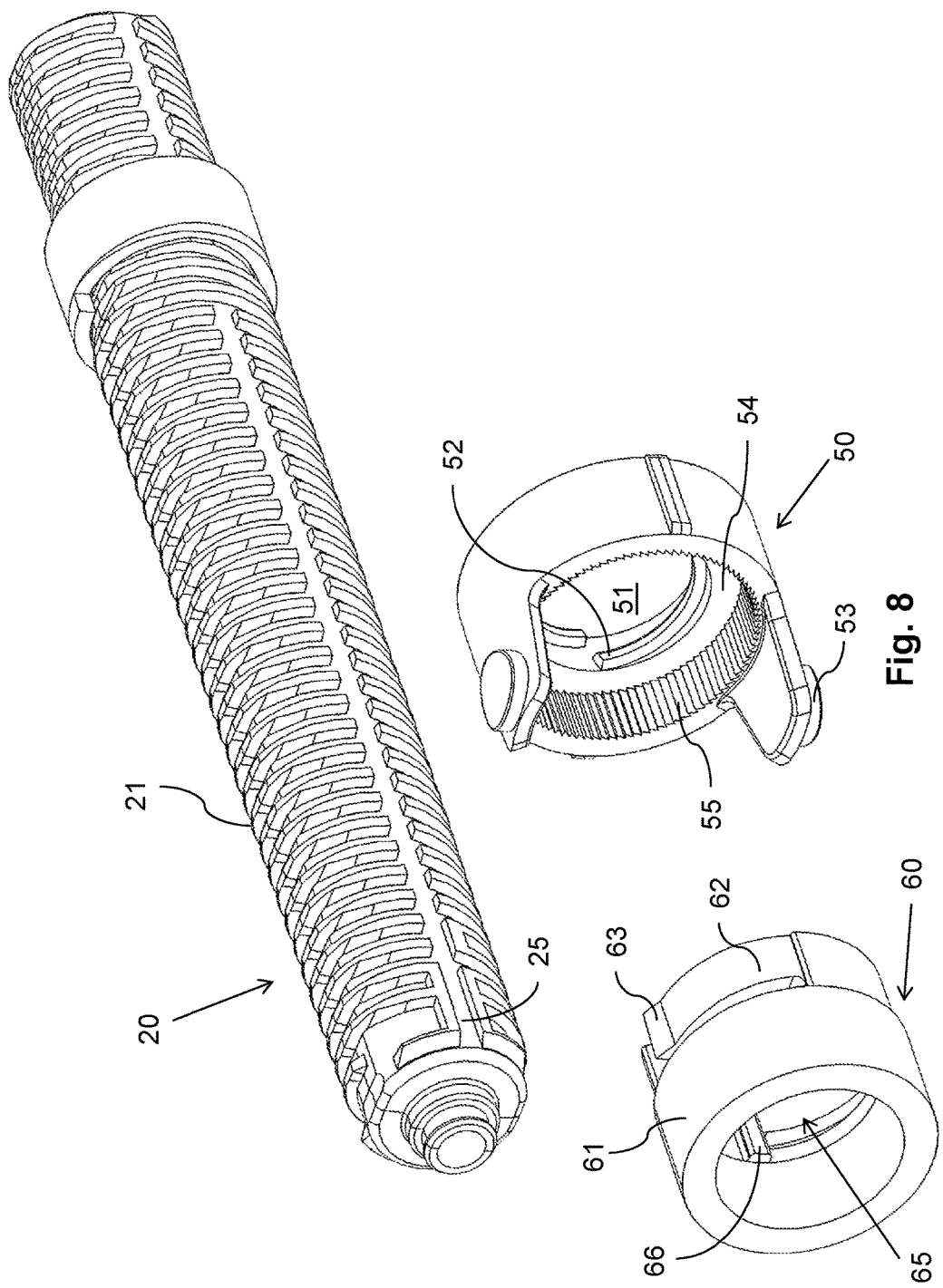
FIG. 8 shows an exploded view of a part of the medicament delivery device according to FIG. 1.

The ratchet 55 cooperates with a ring-shaped back rotation blocker 60 (FIG. 8) which is arranged with two oppositely positioned arms 62, extending along the outer circumferential surface 61 of the back rotation blocker 60. Although two such arms 62 are shown in FIG. 8, a single arm may also suffice. More that two arms could also be provided, depending on the size of the blocking member 60. The arms 62 are flexible in the radial direction. On the radially outwardly directed surfaces of the arms 62, a ledge 63 is arranged. Each ledge 63 has a shape complementary to the ratchet 55 of the thread insert 50. The back rotation blocker 60 is further arranged with a central passage 65 (FIG. 8) through which the plunger rod 20 extends. The central passage 65 is arranged with radially inwardly directed protrusions or ribs 66, which ribs 66 fit into the elongated grooves 25 on the outer surface of the plunger rod 20. Since the thread insert 50 is fixed to the tubular member 10, this structure provides a rotational lock of the plunger rod 20 in one direction because the ledges 63 of the arms 62 engage the ratchet 55, but allows rotational motion in the other direction. The ribs 66 allow axial movement of the plunger rod 20 in the longitudinal direction. The plunger rod 20 may therefore propagate proximally if it rotates relative to the thread insert 50, through the threaded central passage 51, but it cannot move distally during dose setting due to the rotational lock of the back rotation blocker 60.

The plunger rod 20 is further arranged with a plurality of longitudinal splines or ribs 23 provided on the inner circumferential surface of the hollow plunger rod 20 (FIG. 6). A drive drum sleeve 30 (FIGS. 5, 9b, 9c) of generally tubular shape is arranged coaxially with, and radially inside, the plunger rod 20. The drive drum sleeve 30 is provided with a distal end wall 31 transversal to the longitudinal axis of the drive drum sleeve 30. The distal end wall 31 has central opening and the drive drum sleeve is hollow in order to receive an actuator rod 70 (FIG. 9a) therein, as will be described below. The proximal end of the drive drum sleeve 30 comprises one or more, preferably two, flexible arms 33 extending in the proximal direction. The arms 33 are flexible in that their proximal ends are radially deflectable upon application of a radial force thereon, as will be describe below. The outer surface of each flexible arm 33 comprises a radially projecting, longitudinally aligned, plunger rod engagement surface 34 for selectively engaging the longitudinal splines 23 on the inner surface of the plunger rod 20. The shape of the surface 34 may generally correspond to the shape of the circumferentially arranged ribs 23 on the plunger rod 20. The inner surface of each flexible arm 33 comprises a step 37 for engagement with a shoulder 77 of the actuator rod 70 when it is located radially inside the hollow drive drum sleeve 30.

The distal end wall 31 forms a coupling element by means of two proximally extending locking arms 35. The locking arms 35 comprise, at their respective outer surface, a locking structure 36, such as a hook, for rotationally locking the drive drum sleeve 30 to the cut-outs 43 of the dose drum 40, although a slight longitudinal play still exists between the dose drum 40 and the distal end wall 31.

The actuator rod 70 comprises a longitudinal rod 71 and a distal push button 72. The push button is intended to act as a contact surface for a finger of a user during drug delivery, for applying a driving force to expel medicament. In line with the description above, the longitudinal rod 71 of the actuator rod 70 is accommodated coaxially with, and radially inside, the hollow drive drum sleeve 30. The actuator rod is always rotationally movable relative to the drive drum sleeve. At its proximal end, the longitudinal rod 71 comprises an engagement structure comprising a circumferential groove 73 (FIG. 9a). Adjacent the groove and in the proximal direction is a knob 74 and in the distal direction a shoulder 77. FIG. 9b shows that the size of the groove 73 and its position on the longitudinal rod 71 in relation to the drive drum sleeve 30 is such that the step 37 of the flexible arms 33 of the drive drum sleeve 30 is received in the groove 73 when no axial force is exerted on the push button 72. In such a state, the flexible arms 33 are not deflected radially outwards, but are in a relaxed state. In the relaxed state, the drive drum sleeve 30 is rotationally movable in relation to the plunger rod 20. The knob 74 prevents the actuator rod 70 from falling out of the drive drum sleeve 30, distally, when no pressure is applied to the push button 72.

The axial length of the actuator rod 70 in comparison to the drive drum sleeve 30 is such that, in the relaxed state of the medicament delivery device, i.e. with the step 37 being received in the groove 73, the proximal surface of the push button 72 is spaced from the distal surface of the distal end wall 31 by a certain gap (FIG. 9b). This gap is maintained when a dose is set by a user and the first part 41 of the dose drum 40, the drive drum sleeve 30 and the resilient spinning means 70 are moved distally. However, as soon as the push button 72 is pushed in the proximal direction, the push button 72 first bridges the gap thereby moving the longitudinal rod 71 in the proximal direction relative to the drive drum sleeve 30. Due to such relative displacement, the shoulder 77 is moved in contact with, and is pressed against, the step 37 of the flexible arms 33, thus deflecting the arms 33 outwardly, moving the engagement surfaces 34 into engagement with the longitudinal splines 23 on the inner surface of the plunger rod 20, thereby rotationally locking the drive drum sleeve 30 to the plunger rod 20.

A spring washer 75 is arranged between the distal end wall 31 of the drive drum sleeve 30 and the push button 72 of the actuator rod 70, and is compressed when the push button is pressurized. When pressure on the push button is released, the actuator rod will be forced back in the distal direction by the spring washer 75, re-establishing the gap of the relaxed state. Consequently, since the shoulder 77 is moved distally, the arms 33 relax and the engagement surfaces 34 are moved out of engagement with the splines 23 of the plunger rod 20, such that the drive drum sleeve 30 is again rotationally movable in relation to the plunger rod 20.

The function of the medicament delivery device will now be described. FIG. 10a shows the medicament delivery device in the initial state, before a dose has been set. The container holder 80, the container 85 and the stopper 29 are not shown.

In order for a dose to be delivered, the device must first be operated to set a dose. In order to set a dose to be delivered the user grips the tubular member 10 and the distally arranged dose setting knob 41a and turns them in relation to each other, where the dose setting knob 41a is turned in the clockwise direction, for example. The turning of the dose setting knob 41a will cause the dose drum 40 to be rotated. Due to the first threaded connection between the helical groove 49 of the dose drum 40 and the spiral ledge segment 16 of the tubular member 10, the rotation will cause the dose drum 40 to move in the distal direction in relation to the tubular member 10. Inside the dose setting drum 40 the dose drum follower 100 will also rotate and "follow" the dose drum 40 distally due to the engagement between the longitudinally extending ribs 44 of the dose drum 40 and the longitudinally extending grooves 104 of the dose drum follower 100. In addition, the dose blocker sleeve 110 rotates since it is rotationally locked to the dose drum follower. However, it moves distally at a lower speed than the dose drum 40 and the dose drum follower 100 since it is connected to the outer thread 21 of the plunger rod 20 via the second threaded connection, whose pitch is lower than the pitch of the first threaded connection. The plunger rod does not rotate since it is rotationally locked in the dose setting direction by the back rotation blocker 60 interacting with the ratchet 55 of the insert 50.

During dose setting, since the dose drum 40 and the dose drum follower 100 are biased towards each other by the resilient holding members 102 interacting with the slanting ledge 42, a tactile and audible feedback signal is perceived by the user as the proximally-facing part 45 of the dose drum slides over the distally-facing part 95 of the stop member 90, as described above.

Further during dose setting, indicia on the dose drum 40 are shown through the window or opening 13 at the distal end 12 of the tubular member 10. The user thus rotates the dose setting knob 41a until the prescribed dose quantity is displayed. If the user sets a too large dose, he/she may simply turn the dose setting knob 41a in the opposite direction, whereby both the dose drum 40 and the drive drum sleeve 30 are turned in the opposite direction until the correct dose has been reached.

The drive drum sleeve 30 rotates with the dose drum 40 because of the engagement of the locking structure 36 with the cut-outs 43 of the dose drum 40.

FIG. 10b shows a cross-sectional view of the medicament delivery device in the state where a priming dose has been set, but before the push button 72 has been pressed. Notably, the track follower 98 of the stop member 90 has moved some distance along the longitudinal track 18 of the tubular member 10. The threaded ring 111 of the dose blocker 110 has also been longitudinally separated from the dose drum follower 100 and the dose drum 40.

If the user should attempt to set a larger dose than prescribed, i.e. a larger than allowed by the device design, the second stop element 46 will abut the first stop element 96. The stop member 90 is rotationally fixed relative to the tubular member 10. Consequently, due to the rotational block provided by the first stop element 96, the dose drum will be prevented from further rotation and distal movement relative to the tubular member 10.

For comparison with the priming dose of FIG. 10b, FIG. 10c shows the device when a full dose has been set.

In order to deliver a dose of medicament, the user presses the proximal end of the device against a dose delivery site, performing a skin penetration in case the delivery member is a needle. The next step is to press the push button 72 at the distal end of the device. This causes the gap to close under the force applied by the user at the push button 72. FIG. 10d shows the device when the push button 72 has been pressed but before the device starts expelling medicament.

The force applied to the push button 72 and the actuator rod 70 brings the drive drum sleeve 30 into engagement with the inner surface of the plunger rod 20, as described above. Secondly, once the gap between the push button 72 and the distal end wall 31 has been reduced, the force on the push button 72 is transmitted to the dose drum follower as a proximal surface of the distal end wall 31 makes contact with a distal end of the distally extending arms 101, thereby urging the dose drum follower 100 in the proximal direction. This proximal force will be transferred to the dose drum 40 due to the holding members 102 of the dose drum follower 100 being pushed proximally against the slanting ledge 42, thereby causing rotation of the dose drum 40 via the first threaded connection, which also leads to a proximal movement of the dose drum 40 relative to the tubular member 10.

Due to the resilience of the resilient holding members 102, which press radially outwards against the slanting ledge 42 of the cut-outs 43, the force applied by the user causes a slight proximal movement of the dose drum follower 100 in relation to the dose drum 40, thereby releasing the pressure of the stop member 90 against the proximally-facing part 45 of the dose drum 40. Therefore, when the dose is expelled, the shaped surfaces of the distally-facing part 95 of the stop member 90 and of the proximally-facing part 45 of the dose drum 40 will not be pushed against each other. Thus no tactile or audible signal will be generated by the undulating surfaces during dose delivery.

Because of the rotational lock between the dose drum 40 and the drive drum sleeve 30, the latter will also rotate. Due to the radial flexing of the arms 33 of the drive drum sleeve 30, the engagement surfaces 34 of the drive drum sleeve 30 will firmly engage the splines 23 of the plunger rod 20.

Thus when the dose drum 40 and the drive drum sleeve 30 rotate, the latter will drive the plunger rod 20 to rotate as well. This direction of rotation will be allowed by the back rotating blocking element 60 due to the design of its arms 62 in contact with the ratchet 55 of the thread insert 50. The plunger rod 20 will thus rotate together with the back rotating blocking element 60, and the ledges 63 of the arms 62 of the back rotating blocking element 60 will slide over the ratchet 55 of the thread insert 50, generating an audible feedback signal that the dose of medicament is being administered. Further the rotation of the plunger rod 20 will cause it to be moved in the proximal direction due to its threaded connection with the thread insert 50, whereby the movement of the plunger rod 20 will urge the stopper 29 in the proximal direction, thereby expelling a dose of medicament through the dose delivery member. During rotation of the plunger rod 20, the dose blocker sleeve 110 also rotates as it is urged to rotate by the dose drum follower 100. The dose blocker sleeve 110 therefore maintains its axial position with respect to the plunger rod, i.e. the dose blocker sleeve 110 rotates together with the plunger rod 20, i.e. they propagate proximally together as the plunger rod 20 rotates through the threaded insert 50. In a manner similar to the dose setting procedure, the dose drum 40 and the dose drum follower 100 move proximally at a higher speed since the dose drum 40 is in the first threaded connection with the tubular member 10 and since the pitch of the first threaded connection is greater than the pitch of the threaded insert 50. The dose has been delivered when the dose drum 40 has moved back to its initial position relative to the dose drum follower 100 and the dose blocker sleeve 110. This also means that the second stop element 46 has returned to the initial angular position relative to the first stop element 96.

Figure 10E:
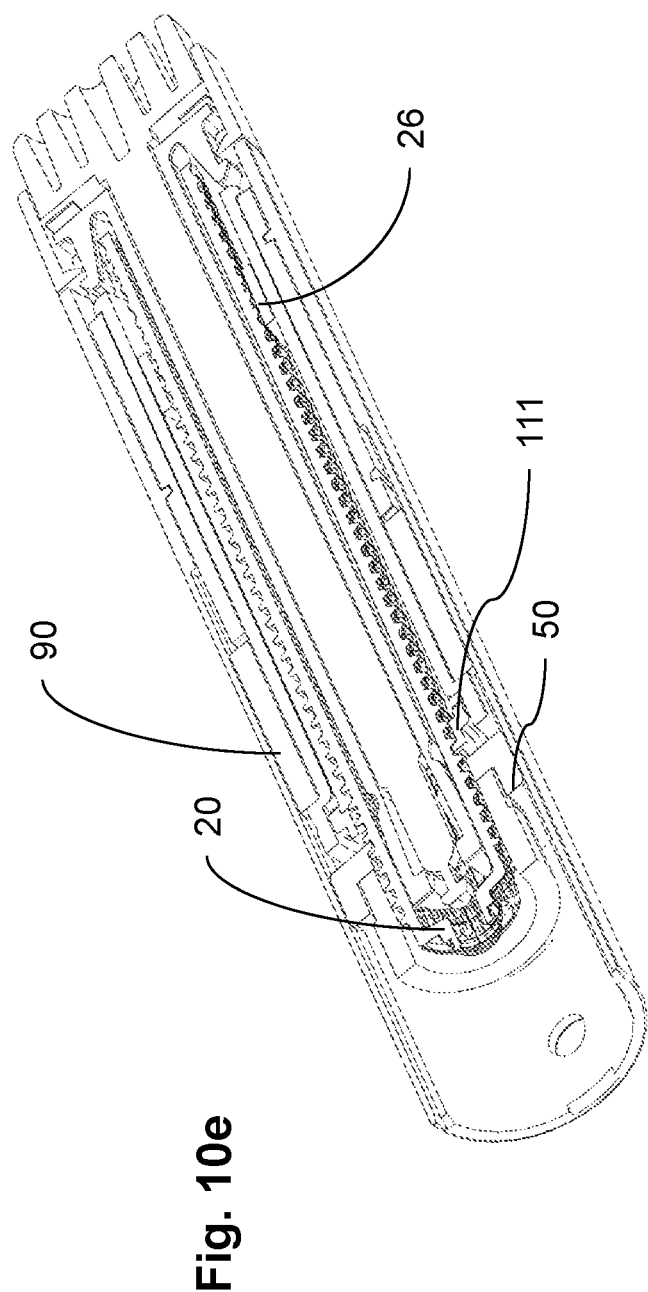

FIG. 10e shows the device after a dose of medicament has been delivered, but before the pressure on the push button 72 has been released. Compared to FIG. 10a, it can be seen that the plunger rod has moved proximally relative to thread insert 50 and to the tubular member 10, and also relative to the dose setting assembly 200. Thus, the second stop element 46 has returned to the initial angular position relative to the first stop element 96 and the dose blocker sleeve 110, comprising the threaded ring 111, is closer to the blocking ring 26 than before the previous dose was delivered.

After dose administration the device is removed from the dose delivery site, and the medicament delivery member is discarded. If the medicament container 85 still contains a large enough dose to be delivered, the above steps may be repeated.

If the medicament container however contains a dose that is smaller than the prescribed dose, the present disclosure prevents setting a dose that is larger than the remaining dose, as previously described.

While the disclosure has been illustrated and described in detail in the drawings and in the foregoing description, such illustration and description are to be considered illustrative or exemplary and not restrictive. It will be understood that changes and modifications may be made, by those of ordinary skill in the art without departing from the spirit of the disclosure.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A dose setting mechanism for a medicament delivery device, which dose setting mechanism comprises:
    a tubular member;
    a dose drum comprising a proximal end face and an outer surface threadedly engaged with an inside surface of the tubular member, and being axially and rotationally movable relative to the tubular member, where the dose drum comprises indicia indicative of a dose of medicament set by a user;
    a stop member having a distal end face, coaxial with the tubular member, and axially movable but rotationally locked relative to the tubular member, and further being axially jointly movable with the dose drum;
    a dose drum follower connected to the dose drum; and
    a dose blocker that is axially movable and rotationally locked to the dose drum follower,
    wherein the stop member comprises a first stop element projecting distally and in that the dose drum comprises a second stop element projecting proximally,
    wherein the distal end face and the proximal end face axially abut each other such that the first stop element and the second stop element interact with each other when the dose drum is rotated relative to the stop member through a predetermined angular interval.

2. The dose setting mechanism according to claim 1, wherein the dose drum is in a first threaded connection with the tubular member.

3. The dose setting mechanism according to claim 2, wherein said stop member is generally tubular and comprises a track follower in engagement with a longitudinal track of the tubular member such that rotational movement of the dose drum causes a rotationally locked, axial movement, of the stop member relative to the tubular member.

4. The dose setting mechanism according to claim 3, wherein the first stop element projects distally from a distally-facing annular end of the stop member and wherein the second stop element projects proximally from a proximally-facing annular end of the dose member.

5. The dose setting mechanism according to claim 4, wherein said predetermined angular interval is defined by an angle between an initial angular position and a full dose angular position of said second stop element relative to the first stop element.

6. The dose setting mechanism according to claim 5, wherein the second stop element abuts the first stop element in said full dose angular position.

7. The dose setting mechanism according to claim 6, wherein a distally-facing part of the stop member and a proximally-facing part of the dose drum are arranged with shaped surfaces such that rotation of the dose drum relative to the stop member causes a tactile and/or audible feedback signal as the shaped surfaces slide against each other.

8. The dose setting mechanism according to claim 7, wherein one of said shaped surfaces comprises a mating segment in a predetermined angular position and wherein the other of said shaped surfaces comprises a corresponding mating segment such that rotation of the dose drum relative to the stop member causes a tactile and/or audible feedback signal as the corresponding mating surface interacts with the mating segment in the predetermined angular position.

9. The dose setting mechanism according to claim 8, wherein the predetermined position of the mating segments corresponds to an intermediate priming position between the initial angular position and the full dose angular position.

10. The dose setting mechanism according to claim 1, wherein the dose drum follower comprises distal, radially resilient holding elements configured to interact with a slanting ledge of the dose drum, the dose drum follower further comprising a proximal support ring such that the stop member is distally biased against the dose drum by the support ring of the dose drum follower through the interaction between the radially resilient holding elements and the slanting ledge.

11. The dose setting mechanism according to claim 10, wherein the stop member is positioned radially outside an elongated half-tubular sleeve of the dose drum follower, and wherein the half-tubular sleeve connects the proximal support ring with a distal forked sleeve of the dose drum follower.

12. The dose setting mechanism according to claim 11, wherein the forked sleeve comprises distally extending arms, which distally extending arms comprise the holding elements, and wherein the distally extending arms are resilient in the radial direction.

13. The dose setting mechanism according to claim 12, wherein the holding elements are arranged with slanting proximal and distal surfaces.

14. The dose setting mechanism according to claim 1, further comprising a threaded plunger rod and a blocking ring, wherein said dose blocker sleeve is in a second threaded connection with the threaded plunger rod, and wherein the blocking ring is fixedly connected to the threaded plunger rod.

15. A medicament delivery device comprising:
a dose setting mechanism comprising,
a tubular member;
a dose drum, coaxial with the tubular member, and being axially and rotationally movable relative to the tubular member;
a stop member, coaxial with the tubular member, and axially movable but rotationally locked relative to the tubular member, and further being axially jointly movable with the dose drum;
wherein the stop member comprises a first stop element projecting distally and in that the dose drum comprises a second stop element projecting proximally, and wherein the first stop element and the second stop element are configured to interact with each other when the dose drum is in an initial position corresponding to a zero dose setting and in a maximum set dose position.

16. A dose setting mechanism for a medicament delivery device, the dose setting mechanism comprises:
a tubular member;
a dose drum rotationally positioned within the tubular member, where the dose drum moves axially and rotationally to the tubular member;
a stop member axially slidable and rotationally fixed to the tubular member through a splined connection;
a drum follower operatively connected to the stop member such that the stop member moves axially with the dose drum;
wherein the stop member comprises a first stop element projecting distally and where the dose drum comprises a second stop element projecting proximally such that the first stop element and the second stop element abut each other when the dose drum is in an initial position corresponding to a zero dose setting and in a maximum set dose position.

17. The dose setting mechanism of claim 16 where the stop member further comprises a distally facing shaped surface that cooperates with a proximally facing shaped surface of the dose drum during dose setting to cause a tactile or audible feedback signal.

18. The dose setting mechanism of claim 16 where the shaped surfaces cooperate to form a priming dose setting.

19. The dose setting mechanism of claim 17 further comprises two first stop element and two second stop elements arranged on opposite sides of the stop member and dose drum, respectively.

* * * * *